(12) United States Patent
Banerjee et al.

(10) Patent No.: US 9,688,686 B2
(45) Date of Patent: Jun. 27, 2017

(54) PORPHYRIN CONTAINING COVALENT ORGANIC FRAMEWORKS AND PROCESS FOR THE PREPARATION THEREOF

(71) Applicant: COUNCIL OF SCIENTIFIC & INDUSTRIAL RESEARCH (AN INDIAN REGISTERED BODY INCORPORATED UNDER THE REGISTRATION OF SOCIETIES ACT (ACT XXI OF 1860), New Delhi (IN)

(72) Inventors: Rahul Banerjee, Pune (IN); Sharath Kandambeth, Pune (IN)

(73) Assignee: Council of Scientific and Industrial Research, New Dehli (IN)

( * ) Notice: Subject to any disclaimer, the term of this patent is extended or adjusted under 35 U.S.C. 154(b) by 0 days.

(21) Appl. No.: 14/900,449

(22) PCT Filed: Jun. 23, 2014

(86) PCT No.: PCT/IN2014/000416
§ 371 (c)(1),
(2) Date: Dec. 21, 2015

(87) PCT Pub. No.: WO2014/203283
PCT Pub. Date: Dec. 24, 2014

(65) Prior Publication Data
US 2016/0376282 A1    Dec. 29, 2016

(30) Foreign Application Priority Data

Jun. 21, 2013 (IN) .......................... 1835/DEL/2013

(51) Int. Cl.
*C07D 487/22* (2006.01)

(52) U.S. Cl.
CPC ........ *C07D 487/22* (2013.01); *C07B 2200/13* (2013.01)

(58) Field of Classification Search
CPC .................................................. C07D 487/22
See application file for complete search history.

(56) References Cited

FOREIGN PATENT DOCUMENTS

| WO | WO-2012/082213 A1 | 6/2012 |
|---|---|---|
| WO | WO-2014/203283 | 12/2014 |

OTHER PUBLICATIONS

"International Application No. PCT/IN2014/000416, International Search Report and Written Opinion mailed Oct. 24, 2014", (Oct. 24, 2014), 11 pgs.
Cao, Yonghai, et al., "Nitrogen-, phosphorous- and boron-doped carbon nanotubes as catalysts for the aerobic oxidation of cyclohexane", *Carbon*, 57, (Jun. 2013), 433-442.
Chen, Xiong, et al., "Toward 2D Conjugated Covalent Organic Frameworks", Abstract, *PMSE Preprints*, vol. 107, (Jan. 2012), p. 352.
Chen, Xiong, et al., "Towards Two-Dimensional Conjugated Covalent Organic Frameworks", *Proceedings, American Chemical Society*, (2013), 1 pg.
Feng, Xiao, et al., "High-Rate Charge-Carrier Transport in Porphyrin Covalent Organic Frameworks: Switching from Hole to Electron to Ambipolar Conduction", *Angew. Chem. Int. Ed.*, 51 (2012), 2618-2622.
Kandambeth, Sharath, et al., "Construction of Crystalline 2D Covalent Organic Frameworks with Remarkable Chemical (Acid/Base) Stability via a Combined Reversible and Irreversible Route", *J. Am. Chem. Soc.*, 134, (2012), 19524-19527.
Kandambeth, Sharath, et al., "Enhancement of Chemical Stability and Crystallinity in Porphyrin-Containing Covalent Organic Frameworks by Intramolecular Hydrogen Bonds", *Angew. Chem. Int. Ed.*, 52, (2013), 13052-13056.
Li, Xin-Hao, et al., "Metal-Free Activation of Dioxygen by Graphene/g-$C_3N_4$ Nanocomposites: Functional Dyads for Selective Oxidation of Saturated Hydrocarbons", *J. Am. Chem. Soc.*, 133(21), (2011), 8074-8077.
Li, Xin-Hao, et al., "Solvent-Free and Metal-Free Oxidation of Toluene Using $O_2$ and g-$C_3N_4$ with Nanopores: Nanostructure Boosts the Catalytic Selectivity", *ACS Catalysis*, 2(10), (2012), 2082-2086.
Li, Yue-Fang, et al., "Graphite as a highly efficient and stable catalyst for the production of lactones", *Carbon*, 55, (2013), 269-275.
Luo, Xu-Zhong, et al., "A Microporous Hydrogen-Bonded Organic Framework: Exceptional Stability and Highly Selective Adsorption of Gas and Liquid", *J. Am. Chem. Soc.*, 135, (2013), 11684-11687.
Neti, Venkata S., et al., "Synthesis of a phthalocyanine and porphyrin 2D covalent organic framework", *CrystEngComm*, 15(35), (Sep. 2013), 6881-7130.
Wan, Shun, et al., "Covalent Organic Frameworks with High Charge Carrier Mobility", *Chem. Mater.*, 23, (2011), 4094-4097.
Wang, Yong, et al., "Boron- and Fluorine-Containing Polymers: Mesoporous Carbon Nitride Polymers: Metal-Free Catalysts for Cyclohexane Oxidation", *Angew. Chem. Int. Ed.*, 49, (2010), 3356-3359.
Xu. Hong, et al., "Catalytic covalent organic frameworks via pore surface engineering", *Chem. Commun.*, 50, (2014), 1292-1294.
Yu, Hao, et al., "Selective Catalysis of the Aerobic Oxidation of Cyclohexane in the Liquid Phase by Carbon Nanotubes", *Angew. Chem. Int. Ed.*, 50, (2011), 3978-3982.

*Primary Examiner* — Brian McDowell
(74) *Attorney, Agent, or Firm* — Schwegman Lundberg & Woessner, P.A.

(57) ABSTRACT

Disclosed herein is novel highly stable, crystalline porphyrin containing covalent organic frameworks and their synthesis using Schiff base reaction which are hydrophobic in nature having good selectivity towards alcohol uptake at low pressure over water. Particularly, present invention provides novel highly stable, porous covalent organic frameworks (COFs) comprising porphyrin linked hydroxyl aromatic compound by intramolecular O—H—N=C bonding; wherein porphyrin is tetra(p-amino-phenyl)porphyrin (Tph) and hydroxyl aromatic compound is selected from group consisting of Triformylphloroglucinol (Tp), 2, 5-dihydroxy-terephthalaldehyde (Da).

7 Claims, 10 Drawing Sheets

Before → After

PORPHYRIN CONTAINING COVALENT ORGANIC FRAMEWORKS AND PROCESS FOR THE PREPARATION THEREOF

PRIORITY CLAIM TO RELATED APPLICATIONS

This application is a U.S. national stage application filed under 35 U.S.C. §371 from International Application Serial No. PCT/IN2014/000416, which was filed 23 Jun. 2014, and published as WO2014/203283 on 24 Dec. 2014, and which claims priority to India Application No. 1835/DEL/2013, filed 21 Jun. 2013, which applications and publication are incorporated by reference as if reproduced herein and made a part hereof in their entirety, and the benefit of priority of each of which is claimed herein.

FIELD OF THE INVENTION

The present invention relates to highly stable crystalline porphyrin containing covalent organic frameworks and their synthesis using Schiff base reaction which are hydrophobic in nature having good selectivity towards alcohol uptake at low pressure over water. Particularly, present invention provides highly stable, porous covalent organic frameworks (COFs) comprising porphyrin linked hydroxyl aromatic compound by intramolecular O—H—N=C bonding; wherein porphyrin is tetra(p-amino-phenyl)porphyrin (Tph) and hydroxyl aromatic compound is selected from Triformylphloroglucinol (Tp) or 2, 5-dihydroxyterephthalaldehyde (Da/Dha). More particularly, present invention provides DaTph/DhaTph COFs having high crystallinity and surface area along with high hydrolytic and acid stability and TpTph COFs having excellent chemical stability (acid/water) and porosity with moderate crystallinity.

BACKGROUND AND PRIOR ART OF THE INVENTION

Covalent organic frameworks (COFs) are a new class of porous materials that follow the same laws of reticular chemistry like Metal-Organic Frameworks (MOFs). They can be synthesized under relatively mild conditions, using reversible condensation reactions like boronic acid trimerisation, boronate ester formation, trimerization of nitriles and Schiff base reaction. The reversibility of the reactions allows the structural units to self-construct until they achieve the long range periodicity, which results in crystallization of COFs. These frameworks exhibit exceptional high surface areas of up to 3000 $m^2 g^{-1}$ and uniform pore size distributions, and hence considered as promising materials for the storage of gases, separation of gas mixtures, catalysis and charge-carrier transport.

In general, two classes of porous COFs are reported; a) chemically stable porous polymeric structures, often called as PAFs/POPs/CTFs etc. with intrinsic porosity but no crystallinity at all, and b) porous COFs with high crystallinity but moderate or poor chemical stability. COFs derived from B—O, C=N bond formation reactions exhibit low chemical stability due to reversible back reactions which leads to decomposition upon exposure to water vapour and limits their effective use in gas storage, (especially $CO_2$) under practical conditions.

Researchers have attempted to rectify these limitations by alkylation of COF pore walls or by pyridine doping. However, these modifications always lead to decrease in the gas adsorption properties even though it enhances the hydrolytic stability to a moderate extent. A microporous hydrogen-bonded organic framework having high stability and selective adsorption of gas and liquid is reopretd by Xu-Zhong Luo in J. Am. Chem. Soc., 2013, 135 (32), pp 11684-11687 Jul. 25, 2013.

The porphyrin based COFs are good conducting COFs with better charge mobility useful in photo or optoelectronic system is reported in the prior art. Article titled, "Covalent Organic Frameworks with High Charge Carrier Mobility" by Wan, S.; in Chem. Mater. 2011, 23, 4094 reported two covalent organic frameworks (COFs) with structures based on covalently linked porphyrin units and their synthesis.

The synthesis comprises condensation reactions between tetra (p-amino-phenyl) porphyrin TAPP and Terephthaldehyde to obtain (a) COF-366, and condensation reactions between TBPP, and THAn to produce (b) COF-66.

Further the said two porphyrin COFs (COF-366 and COF-66) are determined to be hole conducting with mobilities as high as 8.1 and 3.0 $cm^2V^{-1} s^{-1}$. Therefore, these multifunctional conducting COFs combine thermal stability, electrical conductivity, high charge mobility, and pore accessibility, which are suitable to design viable plastic electronics and optoelectronic systems.

Omar M. Yaghi in FY 2010 Annual Progress Report discloses synthesis of porphyrin containing COF (UCLA) by imine condensation of tetra(4-aminophenyl)porphyrin with terephthaldehyde to obtain a new porphyrin COF (termed COF-366). Particularly the process for preparation of COF-366 comprises reaction of tetra (4-aminophenyl) porphyrin and terephthalaldehyde in a solvent mixture of ethanol/mesitylene/acetic acid were placed in a pyrex tube. The tube was sealed at 77 K and under vacuum, and heated at 120° C. for three days. The obtained purple powder was washed with absolute ethanol and immersed in anhydrous tetrahydrofuran for 24 h. The solvent was removed under vacuum at room temperature, yielding a porous COF material (yield: 79% based on the porphyrin).

Sharath Kandambeth et al. in J. Am. Chem. Soc., Nov. 15, 2012, 134 (48), pp 19524-19527, discloses synthesis of two chemically stable [acid and water] 2D crystalline covalent organic frameworks (COFs) (TpPa-1 and TpPa-2) using combined reversible and irreversible organic reactions. The said syntheses of these COFs were done by the Schiff base reactions of 1,3,5-triformylphloroglucinol (Tp) with p-phenylenediamine (Pa-1) and 2,5-dimethyl-p-phenylenediamine (Pa-2), respectively, in 1:1 mesitylene/dioxane. Further TpPa-1 and TpPa-2 showed strong resistance toward acid (9N HCl) and boiling water. Moreover, TpPa-2 showed exceptional stability in base (9N NaOH) as well.

Further Xiao Feng in Angewandte Chemie International Edition Volume 51, Issue 11, pages 2618-2622, Mar. 12, 2012 describes a two-dimensional porphyrin covalent organic framework which allows high-rate carrier transport through the porphyrin columns. Also the Synthesis of a phthalocyanine and porphyrin 2D covalent organic framework is reported by Venkata S. Pavan K. Neti et al. in Cryst Eng Comm, 2013, 15, 6892-6895, 31 May 2013.

Since 2D porphyrin-containing COFs have been reported to show high-rate charge carrier conduction and photoconductivity because of the long-range p-orbital overlapping of porphyrin units, the inventors therefore use this keto-enamine COF formation reaction strategy to synthesize chemically stable and crystalline porphyrin-containing COFs. However, this keto-enamine COF formation strategy to synthesize porphyrin-containing COFs may result in the formation of a 3D architecture. Moreover since the proton tautomerism step is an irreversible phenomenon, the chance of the increment of amorphous content in this 3D porphyrin-based COF is much higher. As a result, there may be much less π-π stacking in this amorphous 3D framework, compared to the crystalline 2D porphyrin-containing COFs.

Hence, in order to enhance the chemical stability and crystallinity in 2D porphyrin COFs, inventors have decided to switch to a new strategy to protect the COF interior by introducing —OH functionalities adjacent to the Schiff base [—C═N] centers in COFs and thereby creating an intramolecular O—H.N═C hydrogen bond. This strategy is used to improve the crystallinity, porosity, and chemical stability of the material. Since porphyrin containing COFs have been reported to show high-rate charge carrier conduction and photo conductivity, the synthesis of chemically stable and crystalline porphyrin containing COFs is the need.

OBJECTIVE OF THE INVENTION

The main object of the present invention is to provide highly stable, porous porphyrin containing crystalline COFs.

Another object of the present invention is to provide highly stable crystalline COFs which are hydrophobic in nature having good selectivity towards alcohol uptake at low pressure over water.

Yet another object of the present invention is to provide a process for the synthesis of COFs having excellent chemical stability in acid or base and porosity along with moderate crystallinity.

Yet another object of the present invention is to provide a process for the synthesis of COFs having high crystallinity and surface area along with high hydrolytic and acid stability.

ABBREVIATIONS USED

Tph: Tetra (p-amino-phenyl)porphyrin or 5,10,15,20-tetrakis(4-aminophenyl)-21H,23H-porphine
Tp: Triformylphloroglucinol
Da/Dha: 2, 5-dihydroxyterephthalaldehyde
TpTph: Stable porphyrin containing covalent organic frameworks of Triformylphloroglucinol
DaTph/DhaTph: Stable porphyrin containing covalent organic frameworks of 2,5-dihydroxy terephthalaldehyde.

For the purpose of this invention, the expression 'DaTph/DhaTph' or 'DhaTph' are used interchangeably throughout the specification and the same may be appreciated as such by the person skilled in the art.

SUMMARY OF THE INVENTION

Accordingly, present invention provides a covalent organic frameworks (COFs) comprising porphyrin linked with hydroxyl aromatic compound by intramolecular O—H—N═C bonding wherein porphyrin used is tetra(p-amino-phenyl)porphyrin (Tph) and hydroxyl aromatic compound is selected from Triformylphloroglucinol (Tp) or 2, 5-dihydroxyterephthalaldehyde (Da/Dha).

In an embodiment of the present invention, the covalent organic frameworks (COFs) is selected from Triformylphloroglucinol linked (tetra(p-amino-phenyl)porphyrin (TpTph) and 2,5-dihydroxyterephthalaldehyde linked (tetra(p-amino-phenyl)porphyrin (DaTph/DhaTph).

In another embodiment of the present invention, the bonding exhibit keto-enamine or enol-imine tautomerism.

In yet another embodiment of the present invention, the intermolecular distance between hydroxyl aromatic group linked to porphyrin is in the range of 1.5 nm to 2.5 nm, preferably 1.8 to 2.0 nm.

In yet another embodiment of the present invention, DaTph/DhaTph COFs having high crystallinity and surface area is in the range of 1300 $m^2$ $g^{-1}$ to 2000 $m^2$ $g^{-1}$.

In yet another embodiment of the present invention, TpTph COFs having moderate crystallinity and excellent porosity (S.A=789 m2/g).

In yet another embodiment of the present invention, TpTph COFs exhibit high hydrolytic and chemical stability (acid or base), and DaTph/DhaTph COFs exhibit high hydrolytic and acid stability in acid for 7 days, wherein the acid is 3N HCl and the base is 3N NaOH.

In another embodiment, present invention provides a process for the synthesis of covalent organic frameworks (COFs), comprising the steps of:
a. mixing hydroxy aromatic compound and porphyrin in the ratio ranging between 2:1 to 1.8:1.2 in the presence of solvent to obtain the reaction mixture;
b. sonicating the reaction mixture as obtained in step (a) for period in the range of 5-15 min to get a homogenously dispersed reaction mixture;
c. freezing the reaction mixture as obtained in step (b) at temperature in the range of 70 to 80K preferably 77K and degassing the frozen mixture followed by heating at temperature in the range of 110 to 130° C. for 3 days to afford the crude product;
d. purifying the crude product as obtained in step (c) to obtain 75-90% product.

In yet another embodiment of the present invention, the solvent used is, dichlorobenzene, alcohol and acetic acid in the ratio ranging between 5:5:1 to 4:4:1 preferably 5:5:1.

In yet another embodiment of the present invention, the alcohol used is selected from the group consisting of methanol, ethanol, isopropanol, n-propanol, tertiary butanol, n-butanol either alone or mixture thereof.

In another embodiment, present invention provides stable, porous DaTph/DhaTph COFs, which exist as enol-imine form due to the strong intramolecular O—H—N═C Hydrogen bonding.

In yet another embodiment of the present invention, the high stability of DhaTph towards acid and water is due to intramolecular O—H.N═C hydrogen-bonding interactions.

In yet another embodiment of the present invention, the porosity and surface area measurements of the acid-treated DhaTph shows a significant change 1305 $m^2$ $g^{-1}$ before and 570 $m^2$ $g^{-1}$ after treatment with acid.

In yet another embodiment of the present invention, highly crystalline and stable COFs of present invention can be used for gas storage and organic photovoltaic applications.

In yet another embodiment of the present invention, the acetic acid used in the process where the concentration is in between 5M-8M preferably 6M.

In yet another embodiment of the present invention, dichlorobenzene and lower alcohol mixture is used in 1:1 ratio.

In yet another embodiment of the present invention, freezing is carried out using liquid $N_2$ bath.

In yet another embodiment of the present invention, degassing is carried out by using three freeze-pump-thaw cycles.

In yet another embodiment of the present invention, the purification of crude product is carried out by known techniques such as chromatography, crystallization, distillation.

In another embodiment, present invention provides a process for the synthesis of porphyrin containing TpTph COFs comprising the steps of:

a) mixing Triformylphloroglucinol (Tp) and tetra(p-amino-phenyl)porphyrin (Tph) in presence of 6M acetic acid, dichlorobenzene and tertiary butanol in ratio (1:5:5) to obtain the reaction mixture;
b) sonicating the reaction mixture of step (a) for 5-15 mints to get a homogenously 0.5 dispersed reaction mixture;
c) freezing the reaction mixture of step (b) at 77K and degassing the frozen mixture followed by heating at 120° for 3 days afforded the crude product;
d) purifying the crude product of step (c) to obtain the desired product as pruple color powder in good yield.

In another embodiment, present invention provides a process for the synthesis of porphyrin containing DaTph/DhaTph COFs comprising the steps of:
a. mixing 2,5-Dihydroxyterephthalaldehyde (Da) and tetra(p-amino-phenyl)porphyrin (Tph) in presence of 6M acetic acid, dichlorobenzene and ethanol (1:5:5) to obtain the reaction mixture;
b. sonicating the reaction mixture of step (a) for 5-15 mints to get a homogenously dispersed reaction mixture;
c. freezing the reaction mixture of step (b) at 77K and degassing the frozen mixture followed by heating at 120° for 3 days afforded the crude product;
d. purifying the crude product of step (c) to obtain the desired product as purple color powder in good yield.

DETAILED DESCRIPTION OF THE INVENTION

The present invention provides highly stable, porous covalent organic frameworks (COFs) comprising porphyrin linked hydroxyl aromatic compound by intramolecular O—H—N═C bonding; wherein porphyrin is tetra(p-aminophenyl)porphyrin (Tph) and hydroxyl aromatic compound is selected from Triformylphloroglucinol (Tp), 2,5-dihydroxyterephthalaldehyde (Da/Dha).

Present invention provides process for synthesis of said highly stable porphyrin containing covalent organic frameworks (TpTph and DaTph/DhaTph) using Schiff base reaction. Both materials are hydrophobic in nature showing good selectivity towards alcohol uptake at low pressure over water. DaTph/DhaTph exist as enol-imine form having high crystallinity and surface area, with high hydrolytic and acid stability. TpTph exist as keto-enamine form having excellent chemical stability (acid/base) and porosity with moderate crystallinity.

The synthesized stable, porous covalent organic frameworks show keto-enamine or enol-imine tautomerism due to intermolecular hydrogen bonding.

The present invention provides stable, porous TpTph COFs which exist as keto-enamine form due to the irreversible keto-enol tautomerism.

The invention provides novel highly stable, porous porphyrin containing covalent organic frameworks of hydroxy aromatic compound/moiety.

The present invention provides novel stable, porous DaTph/DhaTph COFs, which exist as enol-imine form due to the strong intramolecular O—H—N=C Hydrogen bonding.

The high stability of DhaTph towards acid and water is due to intramolecular O—H.N=C hydrogen-bonding interactions.

The porosity and surface area measurements of the acid-treated DhaTph shows a significant change 1305 m$^2$ g$^{-1}$ before and 570 m$^2$ g$^{-1}$ after treatment with acid.

Highly crystalline and stable COFs of present invention can be used for gas storage and organic photovoltaic applications.

Experimental

Experimental date taken from (*Angewandte Chemie International Edition* Volume 52, Issue 49, pages 13052-13056,)

The hydrogen bonding in DhaTph enhances its crystallinity and porosity and stability. To validate this result, inventors were synthesized the methoxy-substituted COE (2,5-dimethoxyterephthalaldehyde linked Tph) i.e DmaTph in which this intramolecular hydrogen bond was not exist. DmaTph was found to have less crystallinity, chemical stability, and porosity compared to DhaTph.

Figure 1:
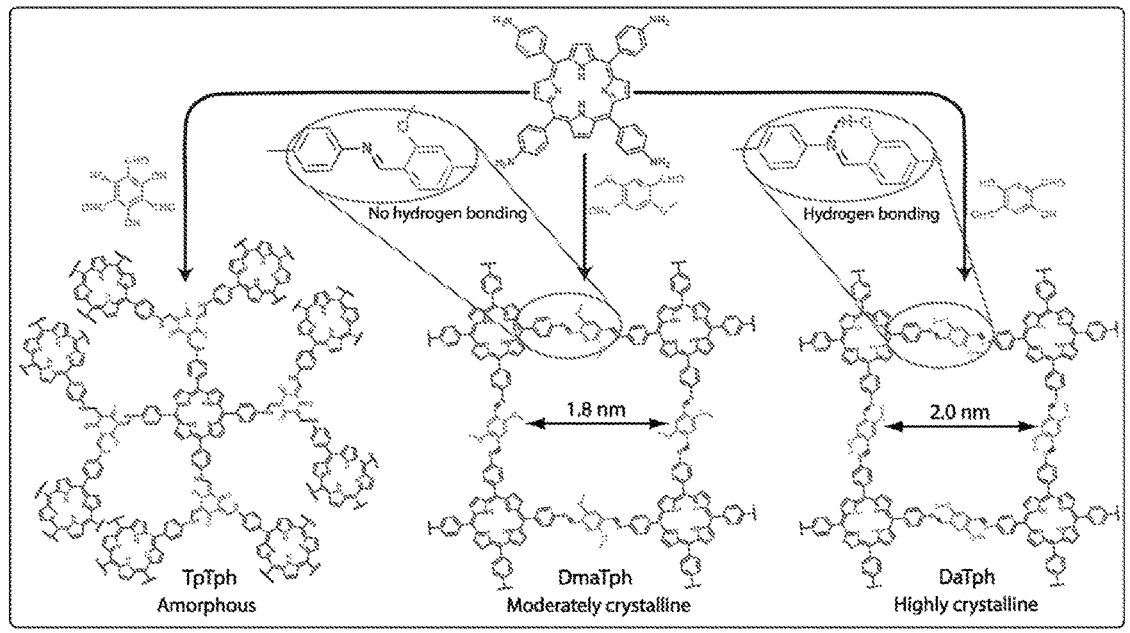
FIG. 1 depicts Schematic representation of synthesis of TpTph, DmaTph and DaTph/DhaTph by the condensation of square planar Tph building unit (blue) with triangular planar Tp, Dma and linear Da building unit (Red).
Figure 2:
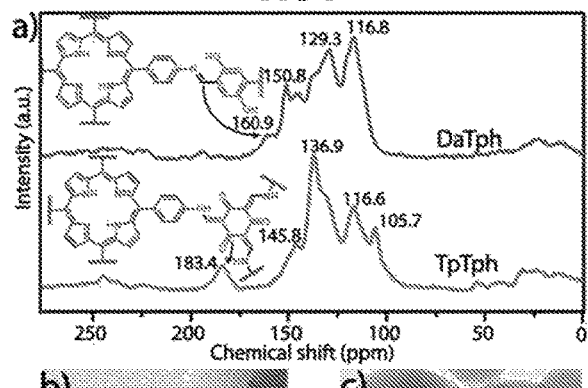
FIG. 2 depicts (a) Comparison of Solid state $^{13}$C NMR of TpTph (Red) and DaTph/DhaTph (Blue). TEM image of (b) DaTph/DhaTph and (c) TpTph showing square shaped and spherical morphology respectively.
Figure 2:
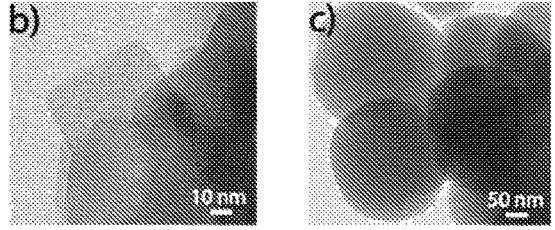
Figure 3:
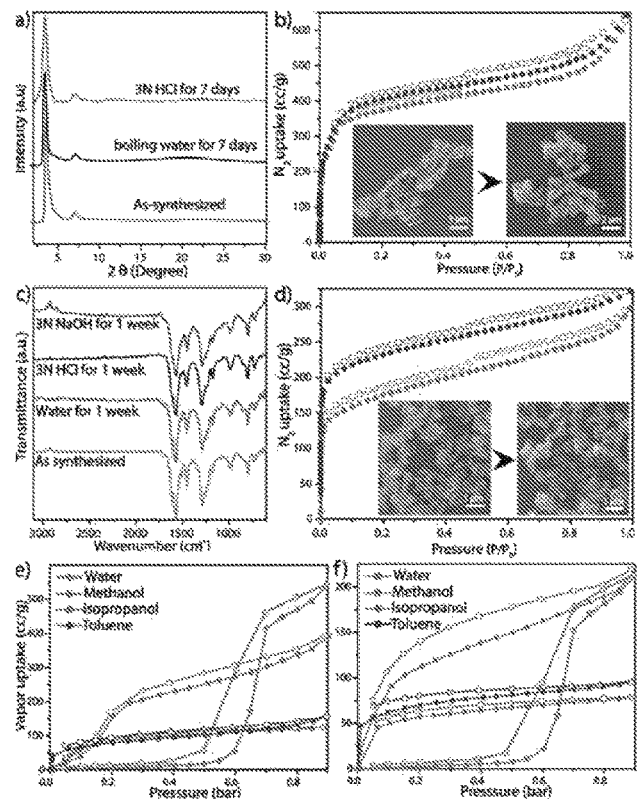
FIG. 3 depicts (a) PXRD pattern showing the stability of DaTph/DhaTph. (b) $N_2$ adsorption isotherms at 77 K of DaTph/DhaTph before (blue) and after treatment with boiling water for 1 week (red). (c) FT-IR showing the stability of TpTph (d) $N_2$ adsorption isotherms at 77 K of TpTph before (blue) and after (red) acid treatment. (e) Vapor adsorption isotherm of DaTph/DhaTph, and (f) TpTph at STP.
Figure 4:
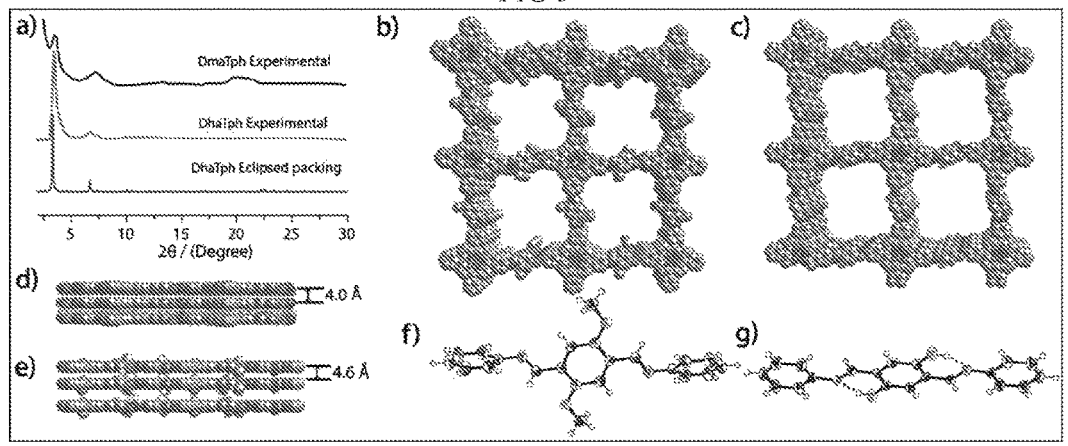
FIG. 4 depicts a) The experimental PXRD pattern of DhaTph (red) compared with simulated eclipsed (blue), PXRD pattern of DmaTph (black) indicates moderate crystallinity. b) Stacking diagram of DhaTph. c) Stacking diagram of DmaTph shows irregular layer stacking. d) Eclipsed stacking model of DhaTph. e) Eclipsed stacking model of DhaTph. f) ORTEP diagram of DmaTph linker unit shows structure is nonplanar. g) ORTEP diagram of DhaTph linker unit shows the presence of the intramolecular hydrogen bond; all atoms are in one plane.
Figure 5:
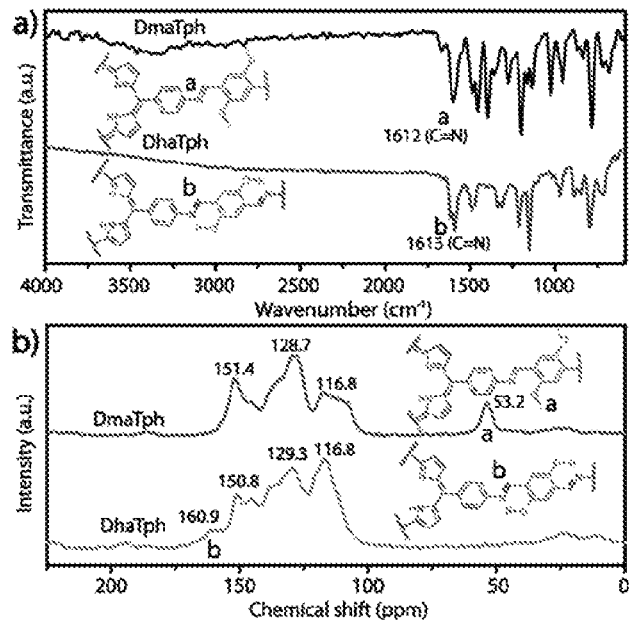
FIG. 5 depicts a) Comparison of FTIR spectra of DmaTph (black) and DhaTph (red). b) Comparison of solid-state 13C NMR spectra of DmaTph (blue) and DhaTph (red).
Figure 6:
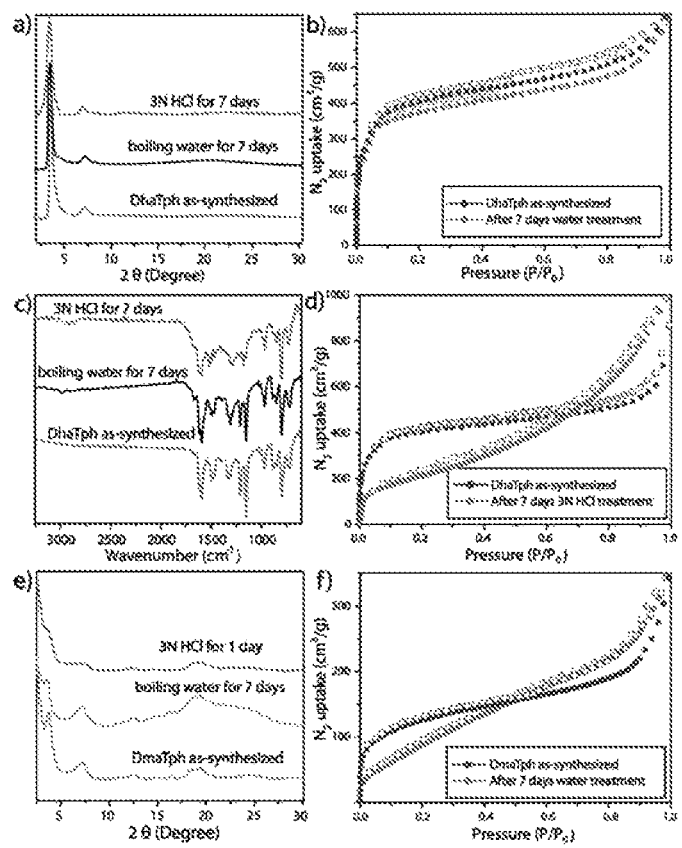
FIG. 6 depicts a) PXRD pattern showing the stability of DhaTph. b) N2 adsorption isotherms at 77 K of DhaTph before (blue) and after treatment with boiling water for 7 days (red). c) FTIR spectra showing the stability of DhaTph. d) N2 adsorption isotherms at 77 K of DhaTph before (blue) and after treatment with 3 n HCl acid for 7 days (red). e) PXRD pattern of DmaTph showing the loss of crystallinity after 1 day. f) N2 adsorption isotherms at 77 K of DmaTph before (blue) and after treatment with boiling water for 7 days (red).
Figure 7:
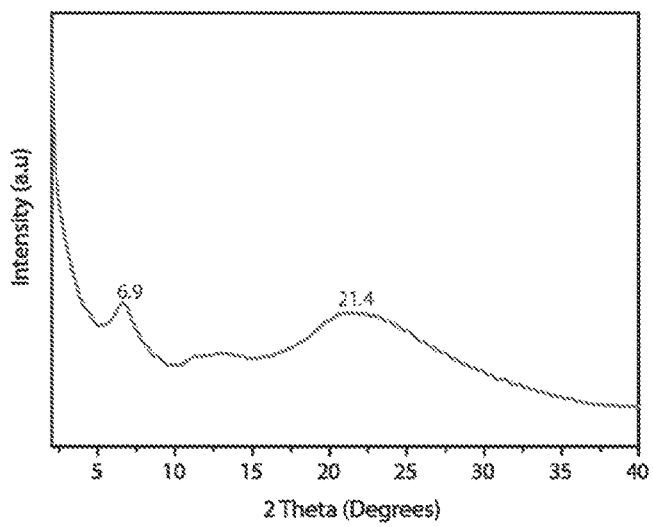
FIG. 7: PXRD pattern of As-synthesized TpTph shows moderate crystallinity.
Figure 8:
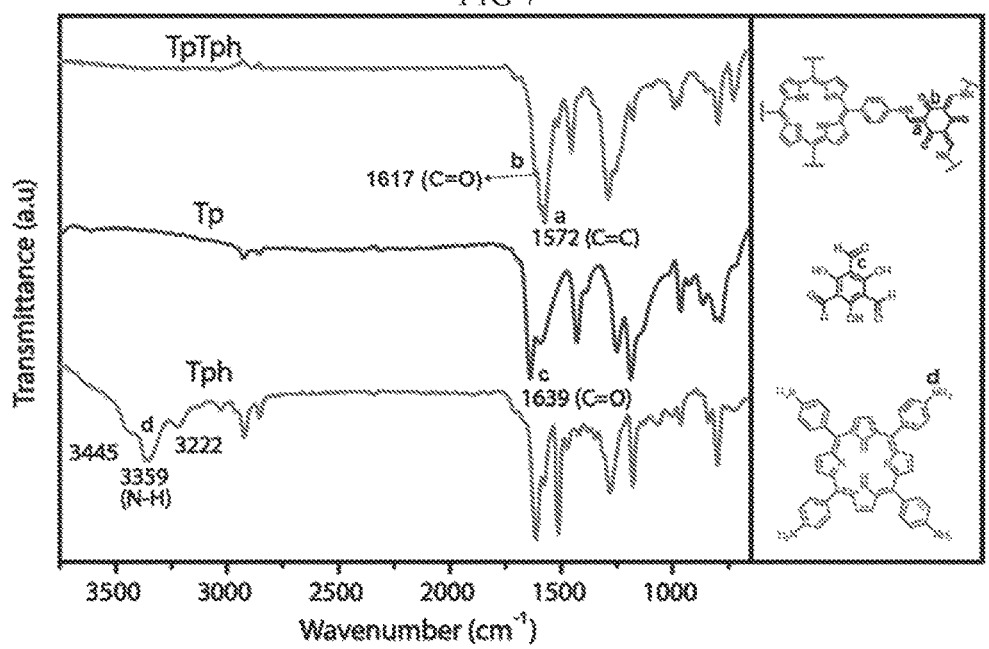
FIG. 8: FT-IR spectra of TpTph (red), 1,3,5-triformylphloroglucinol (Tp) (red accent), and 5,10,15,20-Tetrakis (4-aminophenyl)-21H,23H-porphine (Tph) (green).
Figure 9:
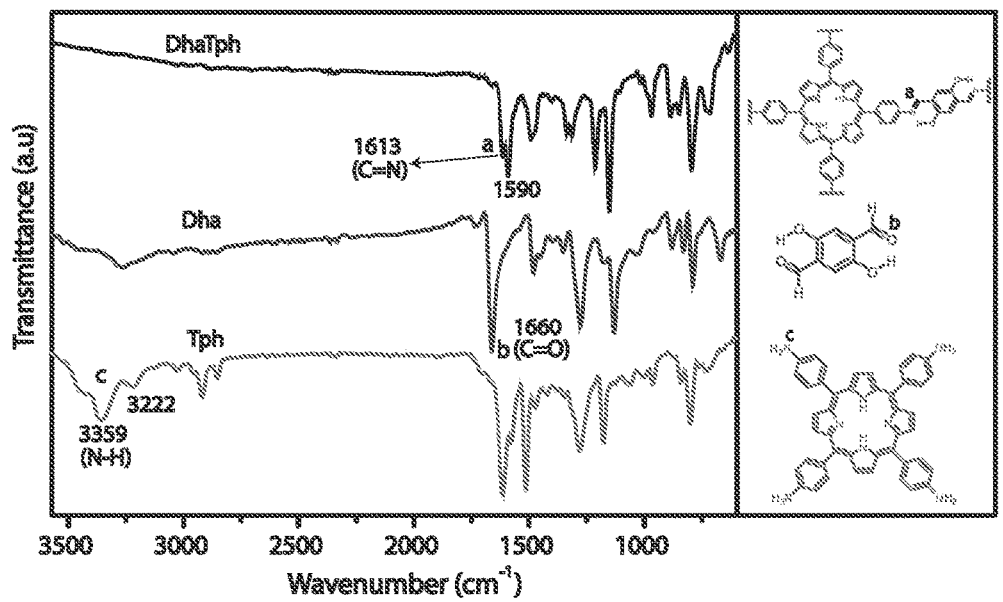
FIG. 9: FT-IR spectra of DhaTph (black), compared with Dha (blue) and Tph (red)
Figure 10:
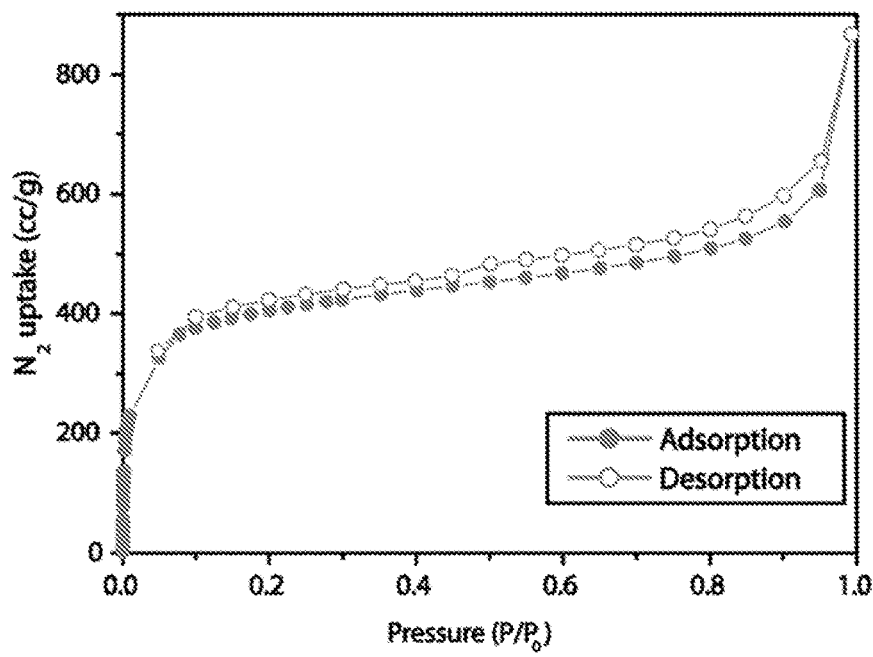
FIG. 10: $N_2$ adsorption isotherm of DaTph/DhaTph.

Syntheses of DmaTph and DhaTph were done by the Schiff base reaction between 2,5-dimethoxyterephthalaldehyde (Dma) (15.5 mg, 0.08 mmol) or 2,5-dihydroxyterephthalaldehyde (Dha) (13.3 mg, 0.08 mmol) and 5,10,15,20-tetrakis(4-aminophenyl)-21H,23H-porphine (Tph) (27.0 mg, 0.04 mmol) in the presence of 6 m acetic acid (0.2 mL) using dichlorobenzene and ethanol (1:1) as the solvent combination (2 mL; FIG. 10). PXRD patterns of DhaTph show a highly intense peak at 3.48 (intensity around 70 000 cps; cps=counts per second) which corresponds to the 100 plane reflections (FIG. 10a).

PXRD patterns of DhaTph also show minor peaks at 6.98 and 20-238 2q which corresponds to the 200 and 001 facets. The p-p stacking distance between COF layers was calculated as 3.8-4.4° A from the d spacing between the 001 plane. PXRD peaks for DmaTph were found to appear almost at the same position to that of DhaTph. Peaks at 3.48, 6.88, and 17-258 correspond to the 100, 200, and 001 facets, respectively. But the peak intensity of the 100 plane (around 3000 cps) has been considerably reduced compared to DhaTph (FIG. 10a). The reason behind this difference in crystallinity among these two COFs is the presence of O—H.N=C intramolecular hydrogen bonding in DhaTph, which holds all phenyl rings in one plane and keeps all imine bonds in the trans conformation. This intramolecular O—H.N=C hydrogen bond, along with the trans —C=N bond, reduces structural defects, and enhances structural rigidity in DhaTph, leading to an improved crystallinity. However, DmaTph does not contain such hydrogen bonding, as the porphyrin (Tph) units are connected by 2,5-dimethoxyterephthalaldehyde units where these —OH functionalities have been replaced by —OCH3 groups. As a result, planarity and structural rigidity between the phenyl rings were lost in DmaTph (FIG. 10f).

This loss in planarity between the phenyl rings decreases the stacking between the 2D layers and subsequently reduces the crystallinity in DmaTph (FIG. 10e). The inventors crystallized the linker units of DhaTph and DmaTph in order to understand the effect of hydrogen bonding on the planarity of the structure (FIGS. 10f and g). It is evident, from the single crystal data, that intramolecular O—H.N=C hydrogen bonding [D=2.619 (2) ° A, d=1.895 (2) ° A, and θ=146.68 (3)] exists in the linker unit of DhaTph and the structure is completely planar (FIG. 10g). However, the DmaTph linker unit is non planar as it does not contain this intramolecular O—H.N=C hydrogen bonding (FIG. 10f).

In order to elucidate the structure of these COFs and to calculate the unit cell parameter, a possible 2D model was built using the self-consistent charge density functional tight-binding (SCCDFTB) method (Chem. Eur. J. 2011, 17, 2388). The experimental PXRD pattern matches well with the simulated pattern of the eclipsed stacking model (FIG. 10b). Hence, inventors propose a structure close to the P4/m space group for DhaTph and DmaTph, after comparing the experimental PXRD pattern with the simulated one (FIG. 10a). The unit cell values of DhaTph and DmaTph were calculated to be (a=b=25.6° A, c=4° A) using the Pawley refinement.

Figure 11:
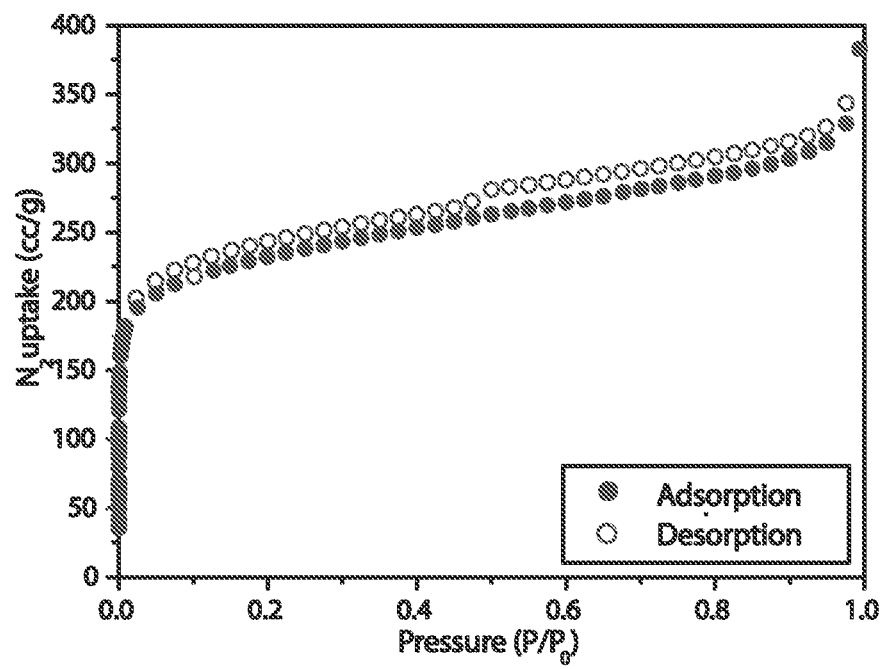
FIG. 11: $N_2$ adsorption isotherm of TpTph.

The total consumption of starting materials, after the COF formation reaction, was indicated by the disappearance of the —N—H stretching bands (3100-3400 cm_1) of Tph and the C=O stretching bands of Dma (1670 cm_1) and Dha (1660 cm_1). in the FTIR spectrum (FIG. 11a). The FTIR spectrum of DhaTph shows characteristic —C=N stretching bands at 1613 cm$^{-1}$, which appear almost at the same position as in the linker unit of DhaTph (1611 cm$^{-1}$; and COF-366 (1620 cm$^{-1}$). Hence, it can be concluded that DhaTph exists in the enol-imine form. For DmaTph, the —C=N stretching band appears around 1612 cm$^{-1}$, which is close to 1613 cm$^{-1}$, the —C=N stretching value of the DmaTph linker unit. The 13C CP-MAS solid-state NMR spectrum of DhaTph confirms the formation of the imine bond by showing the characteristic signal at d 160.9, which corresponds to the chemical shift of the —C=N carbon. These values are close to the chemical shift of —C=N (d 161.8) in the linker unit of DhaTph. To provide supporting evidence for the existence of the enol-imine form, inventors have crystallized the compound 2,5-bis((E)-(phenylimino) methyl)-benzene-1,4-diol) and (2,5-dimethoxy-1,4-phenylene)bis(N-phenylmethanimine) (linker unit present in DhaTph and DmaTph) by the Schiff base reaction between Dha/Dma and aniline. From the single-crystal data, it was evident that the compound exists only in the enol-imine form, which was reflected in the structure of DhaTph and DmaTph (FIGS. 10f and g). The desired enol-to-keto tautomerism was not observed in DhaTph because of the absence of polarized molecules in the system. The 13C cross-polarized magic angle spinning (CP-MAS) solid-state NMR spectrum of DmaTph is almost similar to that of DhaTph but contains an extra signal in the up-field region around d 53.2, which corresponds to the —OCH3 group (FIG. 11b).

TEM images revealed that DhaTph is composed of well-defined, square shaped particles that have a uniform size of around 50 nm. DmaTph particles were much more elongated in shape, forming rectangular or belt-shaped structures (width up to 50 nm and length more than 200 nm).

Thermogravimetric analysis (TGA) was done on activated DhaTph and DmaTph to determine the thermal stability and to confirm the absence of guest molecules inside the pores. Both COFs show thermal stability up to 300° C. A gradual weight loss of 50% for DhaTph and 40% for DmaTph was observed after 300° C. because of the decomposition of the framework. Permanent porosity of DhaTph and DmaTph were evaluated by the N2 adsorption isotherm.

Both DhaTph and DmaTph show a reversible type IV adsorption isotherm with H3 hysteresis.

A sharp rise occurs in the initial state of the N2 adsorption isotherms (0-0.1 bar) because of the filling of small pores, followed by gradual uptake over the remaining pressure range (FIGS. S15 and S18). The steep increase of N2 uptake shown at high relative pressure (P/P0>0.8)) was due to the condensation in the inter particle voids. The surface area of the COFs reported herein has been calculated with the application of the Brunauer-Emmett-Teller (BET) model, and found to be 1305 $m^2 g^{-1}$ for DhaTph and 431 $m^2 g^{-1}$ for the methyl-substituted DmaTph. The improved surface area of the DhaTph compared to DmaTph and COF-366 (735 $m^2 g^{-1}$) can be considered as a result of the improved crystallinity of this material because of the strong intramolecular O—H.N=C hydrogen bond. The value is also comparable with CuP-TFPh50, in which a higher crystallinity and surface area value were obtained as a result of a self-complementary π-π interaction (X. Chen, et al J. Am. Chem. Soc. 2013, 135, 546.).

The lower surface area value for the DmaTph was a result of its moderate crystallinity, together with the incorporation of bulky methyl group towards the pore walls. Langmuir surface areas calculated for both the COFs also show a similar trend: DhaTph has a higher Langmuir surface area (1900 $m^2 g^{-1}$) than DmaTph (740 $m^2 g^{-1}$). The NLDFT model was used to study the pore size distributions. The pore size distribution plot of DhaTph shows a peak maxima at 2.0 nm and a pore volume of 0.809 $cm^3 gm^{-1}$ which is close to the theoretically calculated pore width of 2.1 nm. The peak maxima for DmaTph appear at a lower value of around 1.5 nm. The $H_2$ uptake of DhaTph and DmaTph was found to be 171 $cm^3 gm^{-1}$ and 78 $cm^3 gm^{-1}$, respectively, at 77 K and a pressure of 1 atm. The CO2 uptake of DhaTph was measured as 65 $cm^3 gm^{-1}$, while DmaTph showed a lower CO2 uptake of 37 $cm^3 gm^{-1}$ at 273 K and a pressure of 1 bar (FIG. S51).

Even though the desired enol-keto tautomerism did not happen in DhaTph, the compound remained stable while directly submerged in water for more than seven days. This observation encouraged inventors to make a detailed investigation of the stability of DhaTph and DmaTph in water, acid, and base.

Water Stability

Figure 12:
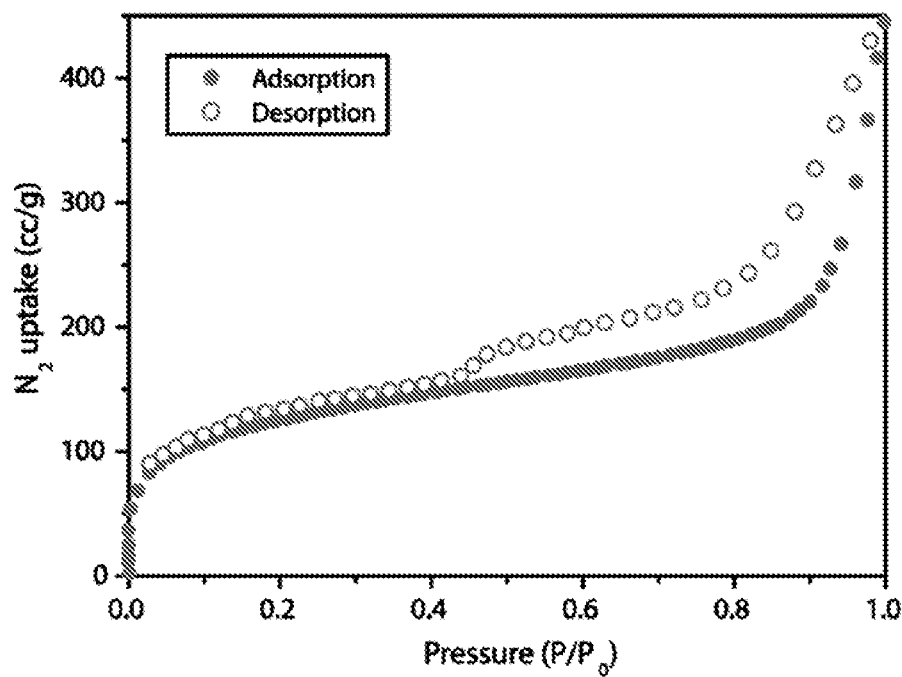
FIG. 12: $N_2$ adsorption isotherm of DmaTph.
Figure 13:
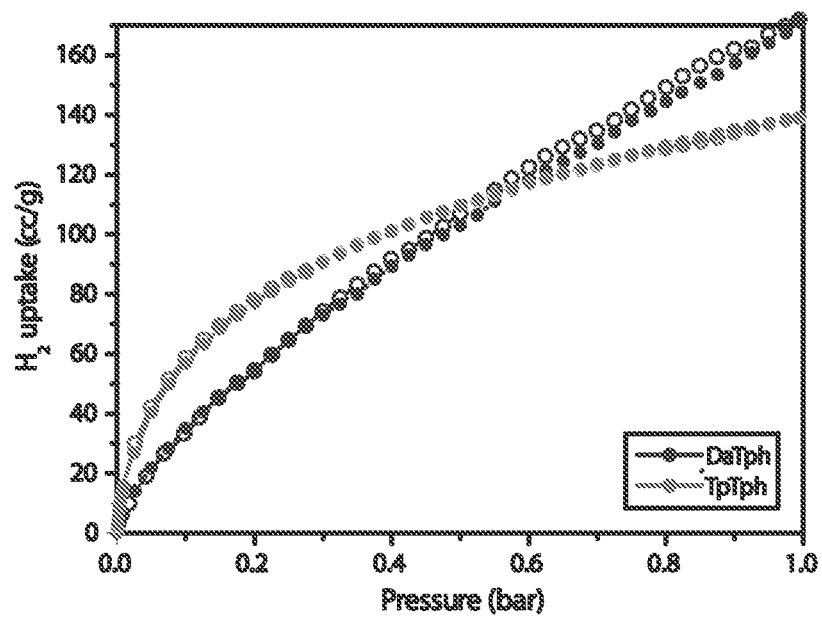
FIG. 13: Hydrogen adsorption isotherms of DaTph/DhaTph (Blue) and TpTph (Red) at 77K.
Figure 14:
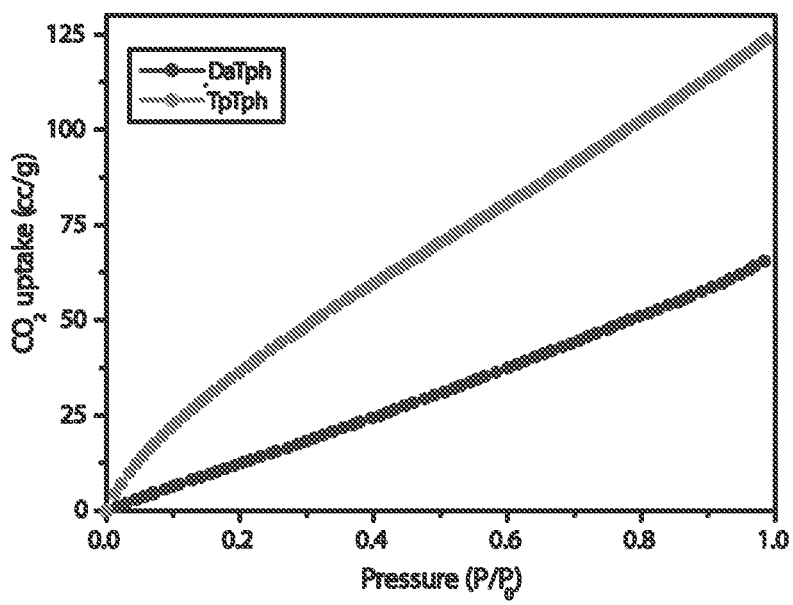
FIG. 14: Carbon dioxide adsorption isotherms of DaTph/DhaTph (Blue) and TpTph (Red) at 273 K.
Figure 15:
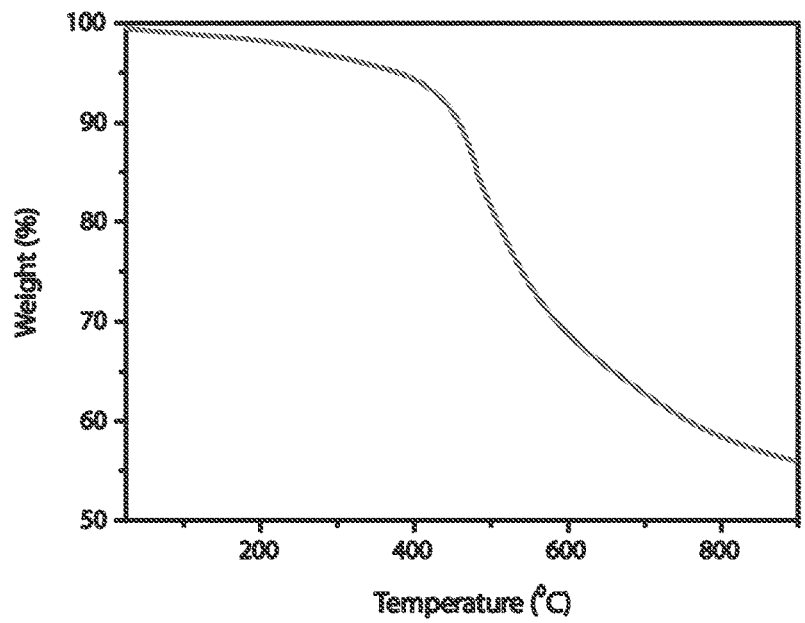
FIG. 15: TGA data of activated COF DaTph/DhaTph under $N_2$ atmosphere.
Figure 16:
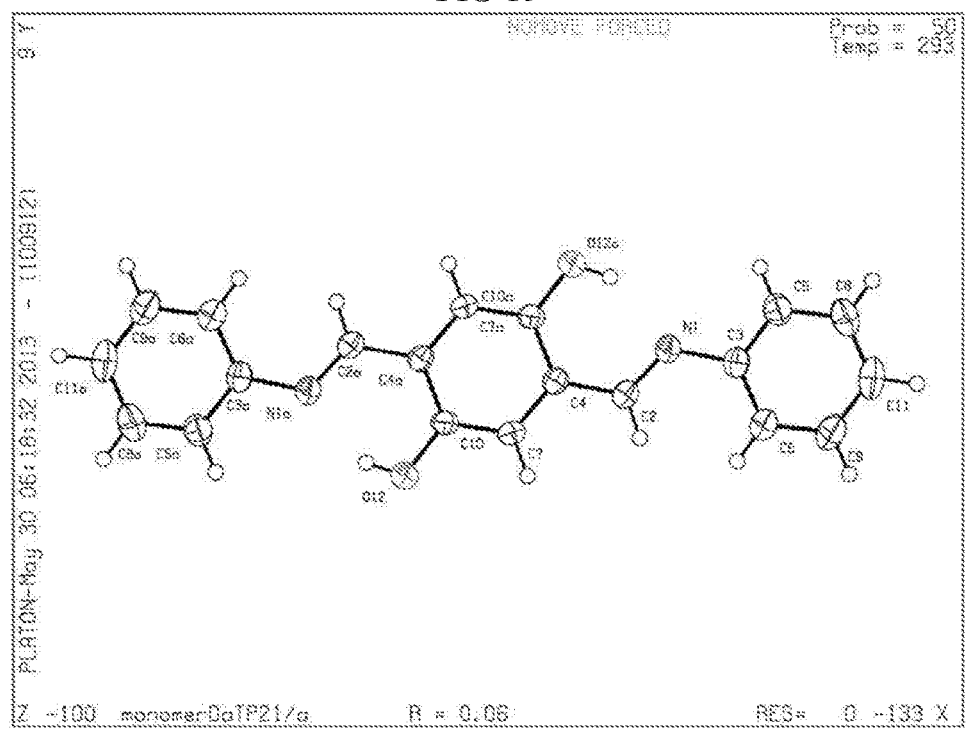
FIG. 16: ORTEP diagram of 2,5-bis((E)-(phenylimino) methyl)benzene-1,4-diol with thermal ellipsoids at 50% probability.
Moiety formula $C_{20}H_{16}N_2O_2$, space group—P2$_1$/a, a=12.2494 (15) Å, b=4.6659 (5) Å, c=14.5554 (19) Å, α=90°, β=113.260 (15)°, γ=90°, V=764.29 (18) Å$^3$, Z=2, Dx=1.375, 3086 reflections measured, 2027 unique reflections, R=0.068, Rw=0.2252. Cambridge Crystallographic Data Centre identifier: CCDC 942020
Figure 17:
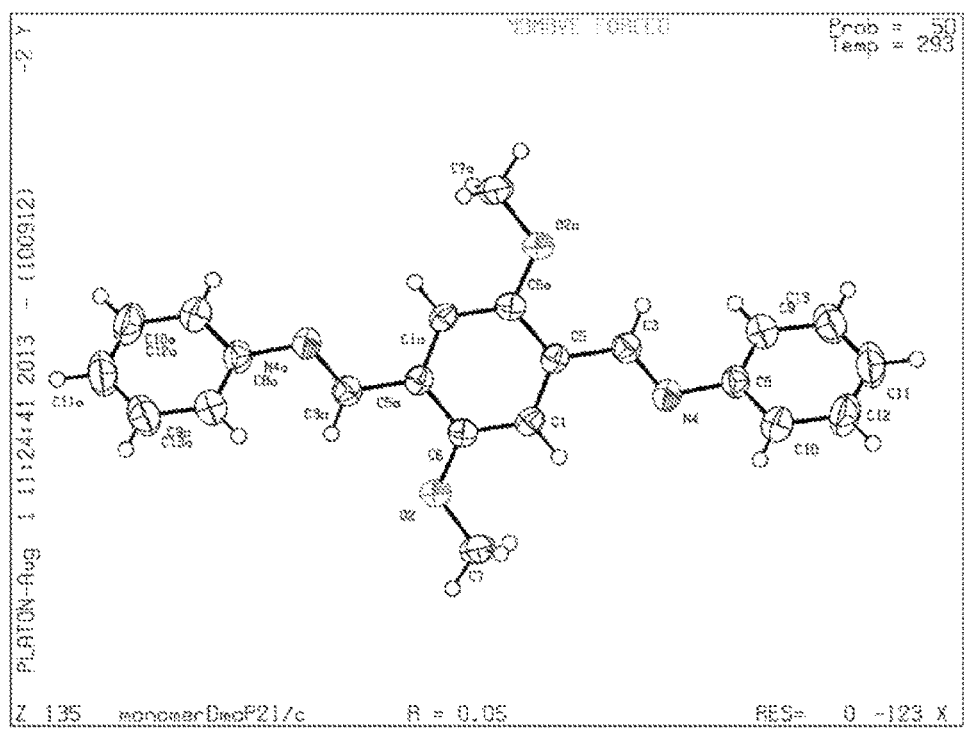
FIG. 17: ORTEP diagram of (1E,1'E)-1,1'-(2,5-dimethoxy-1,4-phenylene)bis(N-phenyl methanimine) with thermal ellipsoids at 50% probability.
Moiety formula $C_{22}H_{20}N_2O_2$, space group—P2$_1$/c, a=16.7895 (18) Å, b=4.3101 (4) Å, c=13.2876 (15) Å, α=900, β=111.657 (13)°, γ=90°, V=893.67 (18) Å$^3$, Z=2, Dx=1.280, 3884 reflections measured, 2425 unique reflections, R=0.0549, Rw=0.1651. Cambridge Crystallographic Data Centre identifier: CCDC 953642
Figure 18:
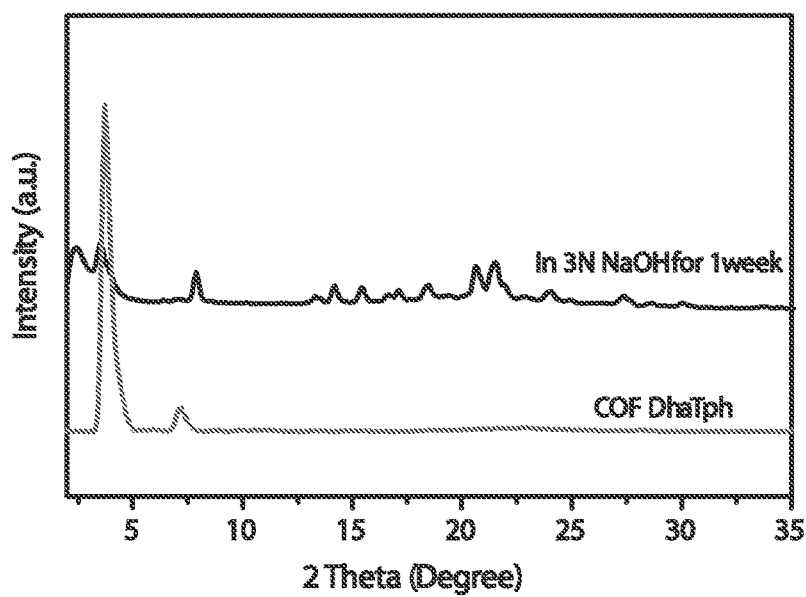
FIG. 18: PXRD of DhaTph/DaTph after treatment with NaOH (9N) for 1 week.
Figure 19:
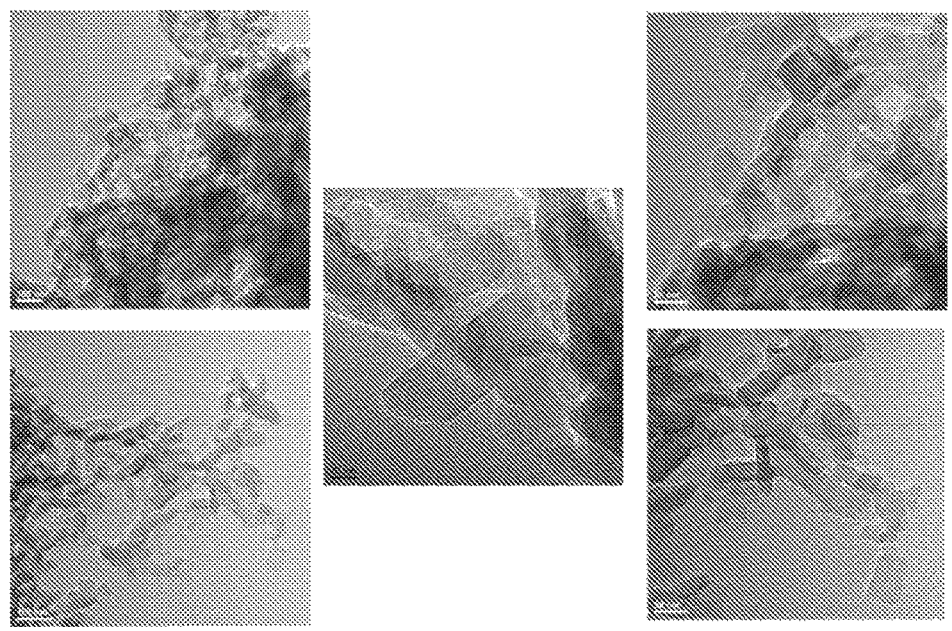
FIG. 19: TEM images of DmaTph.
Figure 20:
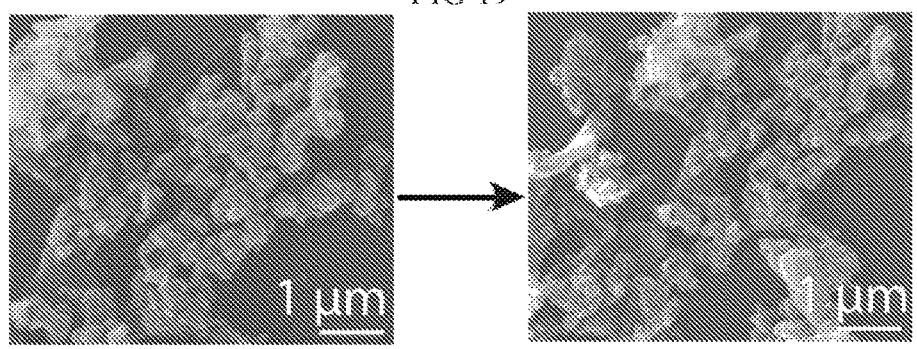
FIG. 20: SEM images of DmaTph before and after acid treatment

To investigate the stability, 50 mg of each COF was directly submerged in 10 mL water and kept boiling for a period of seven days. After this time period, COF powders were filtered, dried, and the retention of crystallinity was tested by PXRD. It was observed that the relative peak intensity and peak position of DhaTph remained identical after this prolonged water treatment (FIG. 12a). The change in porosity (1305 $m^2 g^{-1}$ before and 1252 $m^2 g^{-1}$ after water treatment) of the material was also negligible, as indicated by the N2 adsorption studies (FIG. 12b). This enhancement of water stability of the DhaTph is extremely important, because similar analogous COFs, such as COF-3667 and CuPPh COF11, need anhydrous organic solvents for washing and purification. The intramolecular hydrogen-bonding interaction is the key factor for this enhanced hydrolytic stability of DhaTph. A similar kind of stability test was conducted on the methoxy analogue DmaTph, in which no intramolecular hydrogen-bonding interaction exists. As anticipated, the crystallinity of DmaTph gets significantly lowered within 24 h, as indicated by the reduced peak intensity in the PXRD pattern (FIG. 12e). $N_2$ adsorption isotherms (FIG. 12f) were collected for the water treated DmaTph samples, and found to be decreased to almost ¼th relative to the synthesized sample [229 $m^2 g^{-1}$].

Acid Stability

To determine the stability in acid, 50 mg of DhaTph and DmaTph was submerged in 3 n HCl for 7 days. An immediate green coloration to the solution was observed initially in both cases. After the acid treatment, COF powders were filtered, washed with adequate amounts of water and ethanol, and finally dried at 90° C. It was found that DhaTph suffers a weight loss of about 5% after the acid treatment, but for DmaTph, almost all the material leached out. It was amazing to see that DhaTph retained its exact crystallinity after this long acid treatment, but the SEM image indicated a minor change in the morphology (FIG. 12a). This experiment confirms that our strategy of protecting the —C=N centers in DhaTph by intramolecular hydrogen bonds was correct, as DhaTph shows high water and acid [3 n HCl for 7 days] stability. The porosity and surface area measurements of the acid-treated DhaTph show a significant change (1305 $m^2 g^{-1}$ before and 570 $m^2 g^{-1}$ after treatment). This decrease in the surface area could be probably due to the protonation of the inner porphyrin core by HCl.

It is well reported in literature that porphyrins upon treatment with hydrochloric acid get protonated. Since COFs sample was washed the with water and activated under vacuum it was found that most of the HCl absorbed inside the COF pores should come out. But when the SEM-EDAX of the activated sample was recorded, it showed the presence of 3-5% chlorine. So it was believed that possible decrease in surface area could be due to the protonation inside the pores.

In addition to this inventors have performed CHN analysis of the COF DaTph/DhaTph before and after acid treatment. It was seen that carbon content of the sample got reduced from 71.2% to 59.2%. This can be probably due to the increase in chlorine content in the material due to the protonation in COFs.

PXRD was recorded for the recovered sample of DmaTph after the acid treatment after 24 h (FIG. 12e). It was seen that most of the PXRD peaks disappeared after the treatment with acid (FIG. 12e).

Base Stability

For the base stability test, the same protocol was followed using 3N NaOH. But this time, almost 70% weight loss occurred to DhaTph and the solution color changed to deep red, which indicates the base instability of the sample.

The high stability of DhaTph towards acid and water is a result of intramolecular O—H.N=C hydrogen-bonding interactions. The labile imine bond nitrogen is protected from hydrolysis because of the strong hydrogen-bonding interaction. The preference for hydrogen-bond formation between the target acceptor and a phenolic —OH group is —C=N>-NO2, —C=O>—P=O, and —F>—CF3 reported in the art. Thus, the O—H.C=N hydrogen-bonding interaction is found to be the strongest, which helps to improve the chemical stability and structural rigidity of the materials. In DmaTph, no such hydrogen bond exists, which results in ready decomposition of DmaTph in the lower pH region, just like other Schiff base polymers (Polym. Chem. 2012, 3, 3045).

EXAMPLES

Following examples are given by way of illustration and therefore should not be construed to limit the scope of the invention.

General Remarks:

Triformylphloroglucinol (Tp) was prepared from Phloroglucinol and 2, 5-dihydroxyterephthalaldehyde (Da) was synthesized by 1,4-dimethoxybenzene. All other reagents and solvents were commercially available and used as received. Powder X-ray diffraction (PXRD) patterns were recorded on a Phillips PANalyticaldiffractometer for Cu K$_\alpha$ radiation ($\lambda$=1.5406 Å), with a scan speed of 1° min$^{-1}$ and a step size of 0.02° in 2θ. Fourier transform infrared (FT-IR) spectra were taken on a Bruker Optics ALPHA-E spectrometer with a universal Zn—Se ATR (attenuated total reflection) accessory in the 600-4000 cm$^{-1}$ region or using a Diamond ATR (Golden Gate). Thermogravimetric analyses (TGA) were carried out on a TG50 analyzer (Mettler-Toledo) or a SDT Q600 TG-DTA analyzer under N$_2$ atmosphere at a heating rate of 10° C. min$^{-1}$ within a temperature range of 30-900° C. SEM images were obtained with a Zeiss DSM 950 scanning electron microscope and FEI, QUANTA 200 3D Scanning Electron Microscope with tungsten filament as electron source operated at 10 kV. The samples were sputtered with Au (nano-sized film) prior to imaging by a SCD 040 Balzers Union. TEM images were recorded using FEI Tecnai G2 F20 X-TWIN TEM at an accelerating voltage of 200 kV. The TEM Samples were prepared by dropcasting the sample from isopropanol on copper grids TEM Window (TED PELLA, INC. 200 mesh).All gas adsorption experiments (up to 1 bar) were performed on a Quantachrome Quadrasorbautomatic volumetric instrument. Solid state NMR (SSNMR) was taken in a Bruker 300 MHz NMR spectrometer and Ligand NMR data were taken in Bruker 200 MHz NMR spectrometer. All measurements were carried out at room temperature on an (JobinYvon Horiba, France) using monochromatic radiation emitted by an AR-laser (514 nm) (NRS 1500 W) operating at 20 mW using 50× long distance objective. The experiment was repeated several times and at different positions to verify the consistency of the measurement. The samples were prepared simply by putting a drop of dispersion of COF materials in isopropanol on a clean piece of Silicon wafer.

Example 1

Synthesis of TpTph

A pyrex tube (o.d.×i.d.=10×8 mm$^2$ and length 18 cm) is charged with Triformylphloroglucinol (Tp) (12.6 mg, 0.06 mmol) and tetra(p-amino-phenyl)porphyrin (Tph) (27.0 mg, 0.04 mmol) in presence of 6M acetic acid (0.2 mL) using dichlorobenzene, tertiary butanol (1:1) as solvent combination (2 mL). This mixture was sonicated for few minutes in order to get a homogenous dispersion. The tube was then flash frozen at 77 K (liquid N$_2$ bath) and degassed by three freeze-pump-thaw cycles. The tube was sealed off and then heated at 120° C. for 3 days. After the reaction the COF powders was filtered out, washed with ethanol and dried under vacuum at 150° C. for 12 hours to give purple colored powder in 85% (30 mg) isolated yield based on Tph. FT-IR (powder): 1617, 1591, 1572, 1454, 1287, 1180, 991, 964, 894, 796, 729 cm$^{-1}$.

Example 2

Synthesis of DaTph/DhaTph

The synthesis of DaTph/DhaTph was carried out by utilizing the same protocol with a mixture of 2,5-Dihydroxy-terephthalaldehyde (Da) (13.3 mg, 0.08 mmol) and tetra(p-amino-phenyl)porphyrin (Tph) (27.0 mg, 0.04 mmol) in presence of 6M acetic acid (0.2 mL) using dichlorobenzene, ethanol (1:1) as solvent combination (2 mL). This mixture was sonicated for 10-15 minutes in order to get a homogenous dispersion. The tube was then flash frozen at 77 K (liquid N$_2$ bath) and degassed by three freeze-pump-thaw cycles. The tube was sealed off and then heated at 120° C. for 3 days. After the reaction the COF powders are filtered out, washed with ethanol and dried under vacuum at 150° C. for 12 hours to give purple colored powder in 79% (28 mg) isolated yield based on Tph. IR (powder, cm$^{-1}$): νmax 1615, 1590, 1491, 1399, 1338, 1313, 1213, 1149, 968, 888, 849, 797, 718.

Example 3

Synthesis of 2,5-bis((E)-(phenylimino)methyl)benzene-1,4-diol (Reference Compound for DaTph/DhaTph)

The reference compound was synthesized by the reaction between 2,5-dihydroxyterephthalaldehyde (Da) (0.100 g, 0.602 mmol) and aniline (0.225 g, 2.408 mmol) in 70 mL ethanol under refluxing condition for 24 h. After this time the solution was cooled to room temperature and the precipitate was collected by filtration, washed with ethanol, and dried under vacuum to give 0.158 g (0.5 mmol, 84%) of a yellow solid. FT-IR (powder): νmax 1616, 1590, 1491, 1399, 1388, 1313, 1454, 1444, 1340, 1287, 1236, 1041 cm$^{-1}$; $^1$H NMR (CDCl$_3$, 200 MHz): δ 12.60 (s, 2H), 8.64 (s, 2H), 7.49-7.29 (m, 10H), 7.10 (s, 2H); $^{13}$C NMR (CDCl$_3$, 50 MHz): δ 161.83, 153.01, 132.85, 129.49, 127.45, 123.38, 121.8, 119.29.

Example 4

Synthesis of DmaTph

The synthesis of DmaTph was carried out by utilizing the same protocol with a mixture of 2,5-dimethoxyterephthalaldehyde (Dma) (15.5 mg, 0.08 mmol) and tetra (p-aminophenyl)porphyrin (Tph) (27.0 mg, 0.04 mmol) in presence of 6M acetic acid (0.2 mL) using dichlorobenzene, ethanol (1:1) as solvent combination (2 mL). This mixture was sonicated for 10-15 minutes in order to get a homogenous dispersion. The tube was then flash frozen at 77 K (liquid N$_2$ bath) and degassed by three freeze-pump-thaw cycles. The tube was sealed off and then heated at 120° C. for 3 days. After the reaction the COF powders are filtered out, washed with ethanol and dried under vacuum at 150° C. for 12 hours to give purple colored powder in 79% (28 mg) isolated yield based on Tph. IR (powder): νmax 1612, 1585, 1498, 1466, 1409, 1370, 1289, 1212, 1148, 970, 883, 851, 798, 736 cm$^{-1}$.

Example 5

Synthesis of (1E,1'E)-1,1'-(2,5-dimethoxy-1,4-phenylene)bis(Nphenylmethanimine) (Reference Compound for DmaTph)

The reference compound was synthesized by the reaction between 2,5-dimethoxyterephthalaldehyde (Dma) (0.100 g, 0.515 mmol) and aniline (0.225 g, 2.060 mmol) in 30 mL ethanol under refluxing condition for 24 h. After this time the solution was cooled to room temperature and the precipitate was collected by filtration, washed with ethanol, and dried under vacuum to give 0.163 g, 82% of a yellow solid. FT-IR (powder): νmax 1615, 1584, 1480, 1458, 1404, 1368, 1200, 1136, 970, 875, 829, 756, 688 cm$^{-1}$; $^1$H NMR (CDCl$_3$, 200 MHz): δ 8.92 (s, 2H), 7.81 (s, 2H), 7.46-7.44 (m, 4H), 7.30-7.28 (m, 6H), 3.99 (s, 6H); $^{13}$C NMR (CDCl$_3$, 50 MHz): δ 155.9, 153.9, 152.4, 129.2, 128.5, 126.1, 121.2, 109.6 and 56.2

Example 6

Structure Modeling and Atomic Coordinates of COFs

Atomic positions and cell sizes of modeled COF layers were optimized using Self-Consistent Charge Density Functional Tight-Binding (SCC-DFTB) Method. Stacking of layers are affected by the Coulomb repulsion between the partial atomic charges in adjacent layers. Hence, we performed Mulliken population analysis for the charges. The adjacent layers were shifted with respect to each other in different directions in order to avoid Coulomb repulsion from charges alike. Several possibilities were considered, however, the best was taken from comparison of simulated PXRD pattern with the experimental. Interlayer separation was also determined from the comparison of PXRD patterns. The fractional coordinates of DaTph/DhaTph is given in Table S1 and DmTph is given in Table S2.

TABLE S1

Fractional atomic coordinates for the unit cell of DaTph/DhaTph
DaTph/DhaTph
Tetragonal-P-1
a = b = 25.6 Å, = 4 Å

|  |  |  |  |
|---|---|---|---|
| C1 | 1.0729 | 0.2461 | 0.3432 |
| C2 | 1.0991 | 0.2846 | 0.5206 |
| C3 | 1.0661 | 0.3195 | 0.681 |
| C4 | 1.0133 | 0.3171 | 0.6628 |
| C5 | 0.987 | 0.2785 | 0.4836 |
| C6 | 1.0203 | 0.2431 | 0.3278 |
| C7 | 1.1567 | 0.2867 | 0.5269 |
| C8 | 0.1842 | 0.2398 | 0.5496 |
| C9 | 1.1595 | 0.1915 | 0.6337 |
| C10 | 0.1965 | 1.156 | 0.6376 |
| C11 | 0.2439 | 0.1824 | 0.5548 |
| N1 | 0.2345 | 0.2322 | 0.5116 |
| C12 | 0.2918 | 1.1568 | 0.5353 |
| C13 | 0.3396 | 0.1829 | 0.5081 |
| N2 | 0.3493 | 0.2333 | 0.502 |
| C14 | 0.3993 | 0.2447 | 0.49 |
| C15 | 0.4247 | 0.1965 | 0.488 |
| C16 | 0.3885 | 1.1592 | 0.4908 |
| C17 | 0.4236 | 0.2935 | 0.4727 |
| C18 | 0.4812 | 0.2957 | 0.4786 |
| C19 | 0.5141 | 0.2607 | 0.318 |
| C20 | 0.5669 | 0.2631 | 0.3358 |
| C21 | 0.5932 | 0.3018 | 0.5148 |
| C22 | 0.56 | 0.3371 | 0.6708 |
| C23 | 0.5074 | 0.3341 | 0.6558 |
| N3 | 0.6441 | 0.3091 | 0.5538 |
| C24 | 0.6788 | 0.2788 | 0.4337 |
| C25 | 0.7346 | 0.2855 | 0.4718 |
| C26 | 0.7586 | 0.3267 | 0.6394 |
| N4 | 0.9362 | 0.2711 | 0.4444 |
| C27 | 0.9014 | 0.3015 | 0.5643 |
| C28 | 0.8457 | 0.2947 | 0.5261 |
| C29 | 0.8116 | 0.3307 | 0.6633 |
| C30 | 0.3960 | 0.3404 | 0.4501 |
| N5 | 0.3458 | 0.348 | 0.4885 |
| C31 | 0.3363 | 0.3979 | 0.4455 |
| C32 | 0.3838 | 0.4243 | 0.3624 |
| C33 | 0.4207 | 0.3887 | 0.3659 |
| C34 | 0.2884 | 0.4235 | 0.4653 |
| C35 | 0.2407 | 0.3974 | 0.4924 |
| N6 | 0.2310 | 0.347 | 0.4981 |
| C36 | 0.1809 | 0.3356 | 0.51 |
| C37 | 1.1556 | 0.3837 | 0.5124 |
| C38 | 0.1917 | 0.4211 | 0.5099 |
| C39 | 0.2870 | 0.4811 | 0.4483 |

TABLE S1-continued

Fractional atomic coordinates for the unit cell of DaTph/DhaTph
DaTph/DhaTph
Tetragonal-P-1
a = b = 25.6 Å, = 4 Å

|  |  |  |  |
|---|---|---|---|
| C40 | 0.2495 | 0.5081 | 0.2678 |
| C41 | 0.2467 | 0.5608 | 0.2617 |
| C42 | 0.2815 | 0.5933 | 0.4298 |
| C43 | 0.3199 | 0.5661 | 0.6052 |
| C44 | 0.3220 | 0.5132 | 0.6144 |
| N7 | 0.2736 | 0.6443 | 0.4042 |
| C45 | 0.3033 | 0.6787 | 0.5354 |
| C46 | 0.2956 | 0.7345 | 0.513 |
| C47 | 0.3311 | 0.7683 | 0.6586 |
| C48 | 0.7687 | 0.2496 | 0.3345 |
| C49 | 0.2539 | 0.7589 | 0.3532 |
| O1 | 0.2155 | 0.7299 | 0.1931 |
| C50 | 0.2933 | 1.0991 | 0.5526 |
| C51 | 0.2582 | 1.067 | 0.3866 |
| C52 | 0.2603 | 1.0141 | 0.3961 |
| C53 | 0.2988 | 0.987 | 0.5717 |
| C54 | 0.3336 | 1.0195 | 0.7396 |
| C55 | 0.3308 | 1.0722 | 0.7332 |
| N8 | 0.3066 | 0.936 | 0.5975 |
| C56 | 0.2769 | 0.9016 | 0.4664 |
| C57 | 0.2846 | 0.8457 | 0.489 |
| C58 | 0.2491 | 0.8119 | 0.3434 |
| C59 | 0.3263 | 0.8213 | 0.6489 |
| O2 | 0.3648 | 0.8503 | 0.809 |
| C60 | 0.8216 | 0.2535 | 0.3585 |
| O3 | 0.8509 | 0.2147 | 0.2046 |
| O4 | 0.7293 | 0.3655 | 0.7932 |

TABLE S2

Fractional atomic coordinates for the unit cell of DmaTph
DmaTph
Tetragonal-P-1
a = b = 25.6 Å, c = 4.6 Å

|  |  |  |  |
|---|---|---|---|
| C1 | 0.7826 | 0.9436 | 0.2805 |
| C2 | 0.8074 | 0.9805 | 0.4889 |
| C3 | 0.7749 | 0.0116 | 0.692 |
| C4 | 0.7209 | 0.0071 | 0.683 |
| C5 | 0.6959 | 0.9706 | 0.4709 |
| C6 | 0.7286 | 0.9383 | 0.2748 |
| C7 | 0.8655 | 0.9865 | 0.4944 |
| C8 | 0.8866 | 0.0374 | 0.4535 |
| C9 | 0.9397 | 0.1034 | 0.4607 |
| C10 | 0.8883 | 0.1245 | 0.3695 |
| C11 | 0.8552 | 0.0833 | 0.3643 |
| C12 | 0.9849 | 0.1347 | 0.5074 |
| C13 | 0.979 | 0.1928 | 0.5122 |
| C14 | 0.0105 | 0.2252 | 0.3108 |
| C15 | 0.0061 | 0.2792 | 0.32 |
| C16 | 0.9693 | 0.3042 | 0.5303 |
| C17 | 0.9367 | 0.2715 | 0.7241 |
| C18 | 0.9419 | 0.2176 | 0.7187 |
| C19 | 0.0026 | 0.3871 | 0.4979 |
| C20 | 0 | 0.4441 | 0.4949 |
| C21 | 0.9523 | 0.4727 | 0.4965 |
| C22 | 0.9527 | 0.5272 | 0.4929 |
| C23 | 0.9996 | 0.5562 | 0.4952 |
| C24 | 0.0472 | 0.5276 | 0.4944 |
| C25 | 0.0468 | 0.4731 | 0.4906 |
| C26 | 0.9972 | 0.6132 | 0.4985 |
| C27 | 0.0362 | 0.1145 | 0.5502 |
| C28 | 0.1044 | 0.0593 | 0.5421 |
| C29 | 0.1238 | 0.1101 | 0.6322 |
| C30 | 0.0822 | 0.1438 | 0.6375 |
| C31 | 0.1346 | 0.0134 | 0.4926 |
| C32 | 0.1135 | 0.9625 | 0.4512 |
| C33 | 0.0604 | 0.8966 | 0.459 |
| C34 | 0.1118 | 0.8754 | 0.3671 |
| C35 | 0.1449 | 0.9166 | 0.3614 |
| C36 | 0.0152 | 0.8653 | 0.506 |
| C37 | 0.9639 | 0.8853 | 0.5486 |

TABLE S2-continued

Fractional atomic coordinates for the unit cell of DmaTph
DmaTph
Tetragonal-P-1
a = b = 25.6 Å, c = 4.6 Å

| | | | |
|---|---|---|---|
| C38 | 0.8957 | 0.9405 | 0.5423 |
| C39 | 0.8763 | 0.8897 | 0.6304 |
| C40 | 0.9179 | 0.8559 | 0.6344 |
| C41 | 0.1927 | 0.0195 | 0.4865 |
| C42 | 0.2174 | 0.0567 | 0.2805 |
| C43 | 0.2713 | 0.0622 | 0.2754 |
| C44 | 0.3041 | 0.0296 | 0.469 |
| C45 | 0.2792 | 0.9925 | 0.6781 |
| C46 | 0.2252 | 0.988 | 0.6871 |
| C47 | 0.3869 | 0.9965 | 0.501 |
| C48 | 0.4439 | 0.9993 | 0.5049 |
| C49 | 0.4733 | 0.9527 | 0.508 |
| C50 | 0.5277 | 0.9527 | 0.5055 |
| C51 | 0.5559 | 0.0005 | 0.507 |
| C52 | 0.5266 | 0.0472 | 0.5099 |
| C53 | 0.4721 | 0.0472 | 0.5051 |
| C54 | 0.6129 | 0.0035 | 0.5041 |
| C55 | 0.0212 | 0.8072 | 0.5111 |
| C56 | 0.9901 | 0.7748 | 0.3072 |
| C57 | 0.9944 | 0.7208 | 0.3169 |
| C58 | 0.0308 | 0.6958 | 0.53 |
| C59 | 0.0632 | 0.7285 | 0.7256 |
| C60 | 0.058 | 0.7825 | 0.7198 |
| C61 | 0.00286 | 0.61299 | 0.49752 |
| C62 | 0.00038 | 0.55749 | 0.49526 |
| C63 | 0.14332 | 0.52331 | 0.49494 |
| C64 | 0.52394 | 0.85647 | 0.50233 |
| C65 | 0.99665 | 0.3873 | 0.49805 |
| C66 | 0.85618 | 0.477 | 0.50248 |
| C67 | 0.47577 | 0.14328 | 0.50362 |
| N1 | 0.9369 | 0.0512 | 0.4993 |
| N2 | 0.9622 | 0.3569 | 0.5426 |
| N3 | 0.0377 | 0.6431 | 0.5426 |
| N4 | 0.0522 | 0.0647 | 0.5086 |
| N5 | 0.0633 | 0.9487 | 0.4976 |
| N6 | 0.9479 | 0.9352 | 0.5086 |
| N7 | 0.3567 | 0.0368 | 0.4574 |
| N8 | 0.6433 | 0.9633 | 0.4589 |
| O1 | 0.903 | 0.4471 | 0.501 |
| O2 | 0.0965 | 0.5532 | 0.4958 |
| O3 | 0.5536 | 0.9035 | 0.5026 |
| O4 | 0.4462 | 0.0963 | 0.5019 |

Example 7

Powder X-Ray Diffraction Analysis (PXRD)

In order to elucidate the structure of these COFs and to calculate the unit cell parameters, possible 2-D models were optimized using Density Functional Tight-Binding method. Several stacking possibilities were considered for reasons reported in the literature. The experimental PXRD patterns are agreeable with the simulated patterns of some near-eclipsed stacking models (FIG. S1 and S41). Hence we propose structures close to Tetragonal space group (P4/m) for DaTph/DhaTph by comparing the experimental and simulated PXRD patterns. Refinements of PXRD pattern were done using Reflex module of Material studio.

Example 8

Enol Form Existence

The calculations (in gas phase) were carried out in B3LYP level of theory, using 6-31G (d) basis set implemented on Gaussian 09 program. Inventors applied constrained geometry parameters to maintain the planarity of the molecules where it was found that there not much energy difference.

(5.59 kCal/mol) between two single molecules in gas phase, which may not be the real case in solid crystalline form. However, including solvent parameters may change the stability of the tautomers, for that it may need more calculation in solvent phase.

| Optimized bond lengths | | |
|---|---|---|
| | Enol-Imine form* | Keto-enamine form** |
| C4-O1 | 1.348 Å | 1.261 Å |
| C4-C1 | 1.392 Å | 1.443 Å |
| C4-C12 | 1.426 Å | 1.470 Å |
| C2-C1 | 1.406 Å | 1.381 Å |
| C2-C3 | 1.451 Å | 1.460 Å |
| C3-N1 | 1.293 Å | 1.289 Å |
| N1-C6 | 1.409 Å | 1.410 Å |
| C14-O2 | 1.348 Å | 1.356 Å |
| C12-C2 | 1.426 Å | 1.452 Å |

*Optimized Energy (gas phase) = −647398.94171475 kCal/mol
**Optimized Energy (gas phase) = −647393.350878 kCal/mol.

ADVANTAGES OF THE INVENTION a. Novel chemically stable COFs.
b. A new approach to enhance the crystallinity and porosity of COFs.
c. COFs are hydrophobic in nature showing good selectivity towards alcohol uptake at low pressure over water.
d. High hydrophobicity and selective alcohol uptake over water can make these material ideal for the usage in energy efficient alcohol-water separation technology to generate fuel-grade alcohols in biofuel industries.

We claim:
1. A covalent organic frameworks (COFs) comprising porphyrin linked with hydroxyl aromatic compound by intramolecular O—H—N═C bonding wherein porphyrin used is tetra(p-amino-phenyl)porphyrin (Tph) and hydroxyl aromatic compound is Triformylphloroglucinol(Tp).
2. The covalent organic frameworks (COFs) as claimed in claim 1, wherein the bonding exhibit keto-enamine or enol-imine tautomerism.
3. The covalent organic frameworks (COFs) as claimed in claim 1, wherein the intermolecular distance between hydroxyl aromatic group linked to porphyrin is in the range of 1.5 nm to 2.5 nm.
4. The covalent organic frameworks (COFs) as claimed in claim 1, wherein TpTph COFs having moderate crystallinity.
5. A process for the synthesis of covalent organic frameworks (COFs) as claimed in claim 1, comprising the steps of:
   a. mixing hydroxyl aromatic compound and porphyrin in the ratio ranging between 2:1 to 1.8:1.2 in the presence of solvent to obtain the reaction mixture;
   b. sonicating the reaction mixture as obtained in step (a) for period in the range of 5-15 min to get a homogenously dispersed reaction mixture;
   c. freezing the reaction mixture as obtained in step (b) at temperature in the range of 70 to 80K and degassing the frozen mixture followed by heating at temperature in the range of 110 to 130° C. for 3 days to afford the crude product; and
   d. purifying the crude product as obtained in step (c) to obtain 75-90% product.

6. The process as claimed in claim 5, wherein the solvent used is, dichlorobenzene, alcohol and acetic acid in the ratio ranging between 5:5:1 to 4:4:1.

7. The process as claimed in claim 6, wherein the alcohol used is selected from the group consisting of methanol, ethanol, isopropanol, n-propanol, tertiary butanol, n-butanol either alone or mixture thereof.

\* \* \* \* \*